United States Patent
Chen et al.

(10) Patent No.: US 11,029,237 B2
(45) Date of Patent: Jun. 8, 2021

(54) SYSTEMATIC DEVICE FOR ABYSSAL SEDIMENT PRESSURE-HOLDING TRANSFER

(71) Applicant: Zhejiang University, Zhejiang (CN)

(72) Inventors: Jiawang Chen, Zhejiang (CN); Jing Xiao, Zhejiang (CN); Jiasong Fang, Zhejiang (CN); Weitao He, Zhejiang (CN); Hao Wang, Zhejiang (CN); Yue Huang, Zhejiang (CN); Wei Wang, Zhejiang (CN); Yuxia Sun, Zhejiang (CN)

(73) Assignee: Zhejiang University, Hangzhou (CN)

( * ) Notice: Subject to any disclaimer, the term of this patent is extended or adjusted under 35 U.S.C. 154(b) by 181 days.

(21) Appl. No.: 16/408,196

(22) Filed: May 9, 2019

(65) Prior Publication Data
US 2020/0355579 A1 Nov. 12, 2020

(51) Int. Cl.
*G01N 1/14* (2006.01)
*G01N 1/38* (2006.01)
*G01N 33/24* (2006.01)
*G01N 1/10* (2006.01)

(52) U.S. Cl.
CPC .............. *G01N 1/14* (2013.01); *G01N 1/38* (2013.01); *G01N 33/24* (2013.01); *G01N 2001/1025* (2013.01)

(58) Field of Classification Search
CPC ... G01N 1/14; G01N 1/38; G01N 33/24; G01N 2001/1025; E21B 47/001; E21B 49/001; E21B 49/08; E21B 49/081
See application file for complete search history.

(56) References Cited

U.S. PATENT DOCUMENTS

| 3,892,130 A * | 7/1975 | Winget ............... G01N 1/12 73/864.62 |
| 5,559,295 A * | 9/1996 | Sheryll ............... G01N 1/12 73/864.63 |
| 2019/0204287 A1* | 7/2019 | Chen ............. G01N 33/18 |
| 2019/0368978 A1* | 12/2019 | Sheryll ............ G01N 1/14 |
| 2020/0011768 A1* | 1/2020 | Dong ............... G01N 1/14 |
| 2020/0131853 A1* | 4/2020 | Wan ............... E21B 25/18 |

* cited by examiner

*Primary Examiner* — Benjamin R Schmitt

(57) ABSTRACT

A sediment pressure-holding transfer device developed based on abyssal sediment fidelity sampler is disclosed, which uses a vacuum pump to discharge a gas in the device, uses a high-pressure pump as a power source to perform a pressurization process, uses gravity of a sample to perform a first transfer, and uses a high-pressure impurity pump and a safety valve to perform a second transfer of a sample mixture, in its structure, a high-pressure-resistant and corrosion-resistant material is used as a main material of the device, the device mainly comprises a mechanical system and a hydraulic system, the mechanical system is used as a main frame of the device and is a basis for ensuring operation of the device; the hydraulic system is used as a core of the device and is a key to ensure success of sediment transfer.

4 Claims, 3 Drawing Sheets

SYSTEMATIC DEVICE FOR ABYSSAL SEDIMENT PRESSURE-HOLDING TRANSFER

TECHNICAL FIELD

The present disclosure belongs to the field of deep-sea equipment technology. The present disclosure relates to a pressure-holding transfer device based on deep-sea samples, and the samples to be transferred involve sediments, water bodies and other substances which can be diluted.

BACKGROUND

At present, the abyss equipment technology is becoming a focus of competition of marine technology worldwide, which represents the top challenges in the field of deep-sea engineering technology, and reflects the level of deep-sea engineering technology of a country. At present, the research of abyss science and technology in China is nearly blank.

Western countries have begun to study marine exploration technology earlier, so they are more mature in terms of ocean exploration technology than other countries. In recent years, China's ocean exploration has gradually begun to be incorporated into the national strategic direction. However, there is still a big gap compared with foreign countries in terms of technology. In the aspect of pressure-holding transfer technology, there are corresponding studies at home and abroad. In foreign countries, there are a number of fidelity sampling, transfer and testing equipment developed by Geotek, which have been successfully applied. In our country, the pressure-holding transfer equipment developed by research institutes such as Zhejiang University is still in the experimental stage. However, these devices all perform a transfer by pressure-holding-cutting method. On the one hand, the structure is more complicated and larger, and on the other hand, the pressure that the device can bear is limited which is lower than 100 Mpa.

The abyss science issue represents one of the forefront fields in the development of marine science. Studying of it is an important opportunity for China to occupy the commanding heights of international marine scientific research. It is important for promotion of the development of China's marine science and the overall scientific innovation strength of the country.

SUMMARY

The present disclosure mainly utilizes a double pressure pump for pressure-holding and transferring work. On the one hand, the high-pressure pump ensures that the whole device is under the pressure corresponding to the sea bed, the pressurization device must meet the pressure requirement, and selected device structure and material must also withstand the required high-pressure; on the other hand, it must ensure that the sample mixture can be smoothly transferred to the culture kettle. The structural design and calculation of the pressure pump must meet the strength requirement and minimize leakage. By designing multiple lines for connection, the sample transfer process is ensured. The first transfer of the sample refers to a transfer from the sediment sampler to the magnetic stirring container by its own weight and the second transfer refers to a transfer of the muddy water mixture to the culture kettle by using a high-pressure pump as the power.

To solve the technical problem, the technical solution of the present disclosure is:

A system involving pressurization by a high-pressure water pump, vertical dropping of the sediment, stirring inside the agitator, transferring the high-pressure impurity pump and pressurizing the inside of the culture kettle is provided, including a high-pressure water pump, a sediment sampler, a pressure-holding cylinder, a butt-joint device, a high-pressure ball valve, a magnetic stirring container, a high-pressure impurity pump, a culture kettle, a vacuum pump, a gas cylinder, a brackets and pipes.

The magnetic stirring container is fixed on the bracket by screw connection, an end cover of the container is connected to the high-pressure ball valve, one end of the butt-joint device is connected to the high-pressure ball valve, and the other end is connected to the pressure-holding cylinder outside the sediment sampler, a convex sheet at an upper end of the butt-joint device is placed near the pressure-holding cylinder ball valve, where the outer diameter of the sheet is smaller than the inner diameter of the petal structure, ensuring that the petal structure can be opened, and the thickness of the sheet should be appropriate to ensure utilization of the sample.

The magnetic coupling transmission, which is a core component of the magnetic coupling drive rotary device, is a transmission device that uses a magnetic material for magnetic coupling transmission. The magnetic coupler uses the principle that the magnetic steel can still attract each other through stainless steel, and a sealing cover is made and fixedly connected with the high-pressure working chamber to form a static sealing cavity, thereby effectively preventing leakage. A rotor made of permanent magnet material is arranged respectively inside and outside the sealing cover, and a magnetic steel ring is formed on the rotor by a small magnetic steel block, and N and S poles of the magnetic steel block are arranged in a staggered manner. Since the magnetic steel has the characteristics of opposite poles attract and same poles repel, the inner and outer magnets are mutually positioned in the axial direction and the rotational direction by magnetic force. When the motor drives the outer rotor to rotate, the inner rotor follows the outer rotor by synchronous rotation, and the inner rotor drives the load shaft in the high-pressure working chamber to rotate by a coupling to achieve the purpose of rotation. The magnetic coupler adopts a transmission mode in which the inner and outer magnetic rotors transmit torque through the sealing cover by magnetic force, and the rotating component rotates completely inside the static sealing cavity of the high-pressure working chamber, and does not protrude outside, completely solving the leakage problem that cannot be overcome by other seals. The high-pressure working chamber is placed in an absolutely closed state without any leakage or pollution.

The sediment sampler is a piston sampler developed by Zhejiang University;

The magnetic stirring device is used for uniformly mixing the culture liquid and the sediment sample to avoid the dynamic sealing problem during the stirring process;

The multi-functional butt joint device has internal and external threads for connecting the pressure-holding transfer device and the sediment pressure-holding sampler, and the upper convex sheet is used for opening the petal structure of the sediment sampler device to ensure smoothness of a drop passage of the sediment.

As an improvement, the sediment sample falls by its own weight into a magnetic stirring container;

As an improvement, the sediment sample and the culture solution are uniformly mixed by a magnetic stirring device that is not interfered by the dynamic sealing;

As an improvement, the pressurized medium uses a microbial culture solution to prevent other liquids from diluting or contaminating the sample;

As an improvement, the first transfer and the second transfer of the sample are performed separately without interference;

As an improvement, the temperature compensation and the sediment sampling are performed by a single system and do not use separate systems.

In the present disclosure, some conventional accessories such as a high-pressure water pump and a vacuum pump can be commercially available products. The culture kettle and the water storage device are mainly processed by a titanium alloy material, which can reduce the wall thickness of the container and enhance the corrosion resistance and sealing property of the container. In order not to cause contamination during microbial culture, the culture kettle is maintained in a sealed environment for the microbial culture solution.

The beneficial effects of the present disclosure are:

(1) The maximum pressure resistance of the sediment pressure-holding device is 100 Mpa. The pressure change during the transfer process is not less than 20%, and the transfer rate can reach 100%, which provides equipment guarantee for the research at 10,000 meters deep in the seabed.

(2) The sediment separate charging transfer technology is used to provide samples for multiple culture studies, so that the samples at 10,000 meters deep in the seabed are prevented from being completely wasted because of a single mistake.

(3) Sediment pressure-holding culture provides technical means for fidelity culture of seabed microorganisms, providing technical support for bioengineering research in China.

(4) The pressure-holding transfer device has a simple structure, small size, reduced operation difficulty, and avoids problems such as high-voltage motors and dynamic sealing that cannot be solved during the transfer process.

Figure 1:
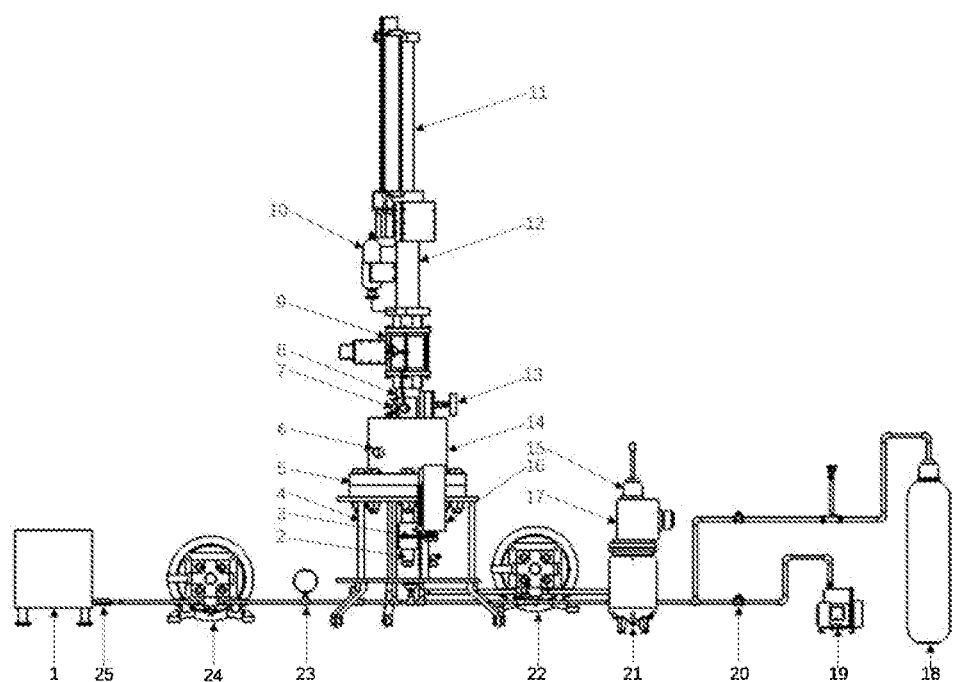
FIG. 1 is a general schematic diagram of a sediment pressure-holding transfer system.

In the drawings: 1—culture liquid tank, 2—magnet steel, 3—belt, 4—bracket, 5—end cap, 6—cooling water port, 7—ball valve, 8—butt-joint sleeve, 9—pressure cylinder port ball valve, 10—accumulator, 11—push rod, 12—pressure cylinder, 13—needle valve, 14—magnetic stirring container, 15—connector, 16—motor, 17—culture ball valve, 18—gas cylinder, 19—vacuum pump, 20—gas control valve, 21—culture kettle, 22—high-pressure impurity pump, 23—pressure gauge, 24—high-pressure water pump, 25—check valve, 26—propeller, 27—sampling cylinder, 28—piston, 29—inlet, 30—bolt, 31—sensor inlet, 32—outlet

DETAILED DESCRIPTION OF EMBODIMENTS

The present disclosure will be further described in detail below with reference to the accompanying drawings and embodiments.

FIG. 1 shows the overall schematic diagram of the sediment pressure-holding transfer system, which mainly comprises a vacuum device, a booster power device, a sampling device, a butt-joint device, a stirring device, and a culture device.

The vacuum device mainly includes a gas control valve 20, a vacuum pump 19, and a gas cylinder 18. The vacuum device is mainly used to discharge the air inside the whole system before the start of test, and to charge the nitrogen with less activity. This cycle is repeated several times to completely discharge the air. The vacuum device is connected to the culture kettle 21 through a gas passage, and the switches between the culture kettle and the other devices are all opened to form a passage for discharging the air inside the device.

The booster power device mainly includes a culture liquid tank 1, a high-pressure water pump 24, a check valve 25, a pressure gauge 23, and pipes. The booster device mainly pressurizes and delivers the culture liquid in the culture liquid tank into the magnetic stirring container and the culture kettle, the water inlet of the high-pressure water pump 24 is connected to the culture liquid tank, and the other end is connected to the magnetic stirring container and the culture kettle through a three-way interface.

The sampling device mainly comprises a pressure cylinder port ball valve 9, an accumulator 10, a push rod 11, a pressure-holding cylinder 12, a sampling cylinder 27, and a piston 28. The device is used for taking the sediment of the seabed with fidelity. The sediment is stored in the sampling cylinder, and is sealed by the petal structure. The push rod 11 can drive the piston 28 to move, thereby moving the sampling cylinder 27 to realize the auxiliary functions of sampling and transferring. The sampling device is connected to the ball valve 7 via a butt joint sleeve 8.

The butt joint device is specially designed for the butt joint sleeve 8 which is adapted to the system. The bottom section has internal thread and is connected with the external thread of the ball valve 7. The middle section has external thread and is connected with the internal thread of the pressure-holding cylinder port ball valve 9. The annular sheet of the upper end is used to open the petal structure of the sampling cylinder.

The stirring device comprises a stirring container and a magnetic stirrer, and is the intermediate core part of the system. The device is the end of the first transfer, the start of the second transfer, and also technical support for the sample changing from solid to liquid mixture. The magnetic stirrer is rotated through rotation of the magnetic steel 2 by the external motor 16 through the belt 3, thereby stirring the rotor 26 of the rotor portion, and uniformly mixing the sediment sample with the culture liquid. A cooling water circulation passage is left in the periphery of the container to maintain the temperature inside the container. A sensor inlet 31 and a water port 32 are left on the end cap.

The culture device is the final destination of the sediment sample. The culture kettle mainly comprises a kettle body 21 and a kettle lid 17. When the sample is successfully transferred to the culture kettle 21, the culture kettle port ball valve 17 is closed to complete the transfer. The culture kettle 21 is a replaceable device, and after one transfer is completed, another empty culture kettle is exchanged until the entire transfer of the sample is completed.

Figure 2:
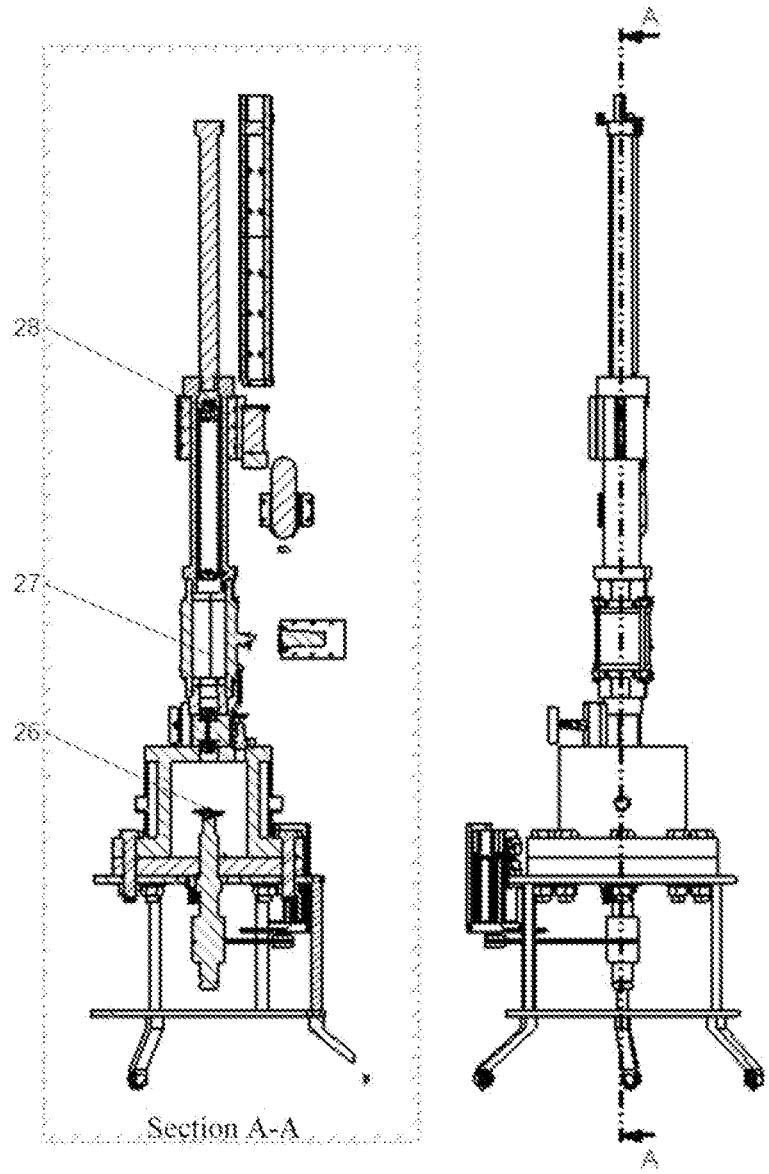
FIG. 2 is a schematic diagram of a first transfer system.
Figure 3:
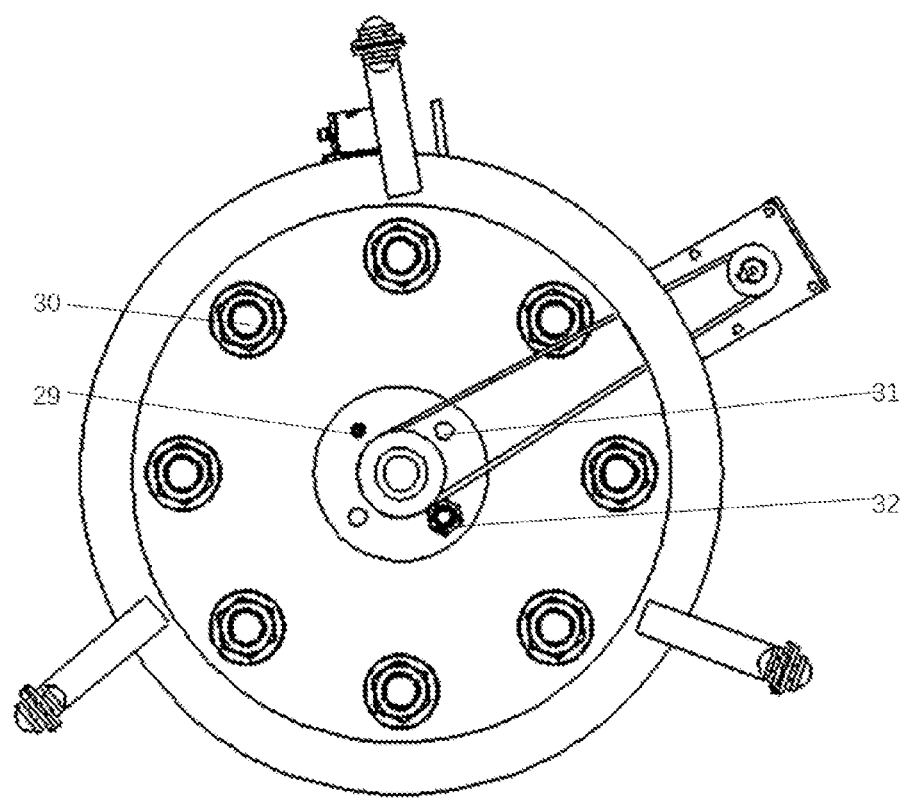
FIG. 3 shows a bottom end of the magnetic stirring container.

FIG. 2 shows the schematic diagram of the first transfer system, which is also the core process of this transfer. Temperature compensation and pressure compensation are controlled in this part. At the same time, the whole transfer process is carried out under invisible conditions, so the sectional view is shown.

The working steps of this embodiment will be described below with reference to the accompanying drawings:

1) Performing butt joint of the sampling device and the pressure-holding transfer device through the ball valve 7;

2) Opening the vacuum pump 19, discharging the air inside the device to make it in a vacuum state, closing the vacuum pump 19, and closing the pipe connected thereto;

3) Turning on the high-pressure water pump 24, pressurizing the magnetic stirring container 14 to 100 MPa, pressurizing the culture kettle 21 to 99.2 MPa, after the pressurization is completed, turning off the high-pressure water pump 24, and turning off the switch on the boosting passage;

4) Opening the connection ball valve 7 between the sampling device and the pressure-holding transfer system, and pushing the piston 28 downward by the structure of the push rod 11 of the sampling device until the petal structure of the sampling barrel is opened by the ring structure built in the pressure-holding transfer device, thereby the sample of the sediment in the sampling tank flowing out into the magnetic stirring container 14 by gravity;

5) Starting the motor 16, driving the magnetic stirrer 2 through the belt 3 by the motor 16, and evenly stirring the culture liquid and the sediment sample;

6) Turning on the high-pressure impurity pump 22, extracting the mixture sample out by the pressure difference between the inlet and the outlet of the high-pressure impurity pump, sending the mixture sample to the culture kettle 21, and when the pressure in the culture kettle 21 reaches 100 MPa and the transfer is finished, turning off the high-pressure impurity pump 22 and the culture kettle port ball valve 17;

7) Removing the culture kettle 21 already sealed, deploying another culture kettle, repeating the above processes, and packing the sample into another culture kettle for study.

We claim:

1. A sediment pressure-holding transfer device, comprising:—a sediment fidelity sampler; wherein the sediment pressure-holding transfer device uses a vacuum pump to discharge a gas in the device, uses a high-pressure pump as a power source to perform a pressurization process, uses gravity of a sample to perform a first transfer, and uses a high-pressure impurity pump and a safety valve to perform a second transfer of a sample mixture, in its structure, a high-pressure-resistant and corrosion-resistant material is used as a main material of the device, the device comprises a mechanical system and a hydraulic system, the mechanical system is used as a main frame of the device and is a basis for ensuring operation of the device; the hydraulic system is used as a core of the device; the mechanical system and the hydraulic system cooperate together to ensure that a sediment sample is smoothly transferred from a sediment sampling cylinder to a culture kettle, the sediment fidelity sampler has a volume of ≥150 ml and a height of ≥100 mm, and is connected with the pressure-holding transfer device by using a ball valve thread interface;

the gas to be discharged refers to air present in a container, and a purpose is to ensure that the sample is not contaminated by other substances in the air during a transfer process, and another purpose is to avoid a danger caused by a poor compression ratio of the gas during the pressurization process; and the pressurization process refers to a continuous filling of a high-pressure liquid into a corresponding container through a high-pressure pump so that a pressure of the container equals to an in-situ pressure of a seabed sample.

2. The sediment pressure-holding transfer device according to claim 1, wherein a pressurized medium used for the pressurization process is a microorganism-specific culture liquid.

3. The sediment pressure-holding transfer device according to claim 1, wherein the main material of the device is Tc4.

4. The sediment pressure-holding transfer device according to claim 1, wherein the transfer process comprises a first transfer and a second transfer, the first transfer refers to a process in which the sediment is transferred from a sampling bucket to the high-pressure magnetic stirring container, the second transfer refers to a process in which a sediment-culture liquid mixture is transferred to the culture kettle.

* * * * *